(12) United States Patent
Wang et al.

(10) Patent No.: US 8,093,035 B2
(45) Date of Patent: Jan. 10, 2012

(54) PSEUDOMONAS SP. STRAIN AND METHOD OF PRODUCING CHITINASE, CHITOSANASE AND NATTOKINASE USING THE SAME

(75) Inventors: San-Lang Wang, Danshui Town (TW); Hsin-Jen Chen, Guanxi Town (TW)

(73) Assignee: Tamkang University, Taipei (TW)

( * ) Notice: Subject to any disclaimer, the term of this patent is extended or adjusted under 35 U.S.C. 154(b) by 548 days.

(21) Appl. No.: 12/272,855

(22) Filed: Nov. 18, 2008

(65) Prior Publication Data

US 2011/0207200 A1 Aug. 25, 2011

(30) Foreign Application Priority Data

Mar. 20, 2008 (TW) ................. 97109902 A (51) Int. Cl.
*C12N 1/00* (2006.01)
*C12N 9/14* (2006.01)
*C12N 9/24* (2006.01)
*C12N 9/68* (2006.01)
*C12N 9/50* (2006.01)

(52) U.S. Cl. ........ 435/243; 435/195; 435/200; 435/217; 435/219

(58) Field of Classification Search .................. 435/243, 435/195, 200, 217, 219
See application file for complete search history.

(56) References Cited

OTHER PUBLICATIONS

Wang et al., 1999: Wang J, Wang M, Wang Y (1999) Purification and characterization of a novel fibrinolytic enzyme from *Streptomyces* spp. Chin. J. Biotechnol. 15: 83-89.
Xiao-Lan et al., 2005: Liu XL, Du LX, Lu FP, Zheng XQ, Xiao J. (2005) Purification and characterization of a novel fibrinolytic enzyme from *Rhizopus chinensis* 12, Appl. Microbiol. Biotechnol. 67: 209-214.
Fujita et al., 1993: Fujita M, Nomura K, Hong K, Ito Y, Asada A, Nishimuro S (1993) Purification and characterization of a strong fibrinolytic enzyme (Nattokinase) in the vegetable cheese natto, a popular soybean fermented food in Japan. Biochem Biophys. Res. Commun. 197: 1340-1347.
Peng et al., 2003: Peng Y, Huang Q, Zhang RH, Zhang YZ (2003) Purification and characterization of a fibrinolytic enzyme produced by *Bacillus amyloliquefaciens* DC-4 screened from douchi, a traditional Chinese soybean food. Comp. Biochem. Physiol. Biochem. Mol. Biol. 134: 45-52.
Kim et al., 1996: Kim W, Choi K, Kim Y, Park H, Choi J, Lee Y, Oh H, Kwon I, Lee S (1996) Purification and characterization of a fibrinolytic enzyme produced from *Bacillus* sp. strain CK 11-4 screened from Chungkook-Jang. Appl. Environ. Microbiol. 62: 2482-2488.
Kim and Choi, 2000: Kim SH, Choi NS (2000) Purification and characterization of subtilisin DJ-4 secreted by *Bacillus* sp. strain DJ-4 screened from Doen-Jang. Biosci. Biotechnol. Biochem. 64: 1722-1725.
Ko et al., 2004: Ko JH, Yan JP, Zhu L, Qi YP (2004) Identification of two novel fibrinolytic enzymes from *Bacillus subtilis* QK02. Comp. Biochem. Physiol. C Toxicol. Pharmacol. 137: 65-74.
Jeong et al., 2001: Jeong YK, Park JU, BaekH, Park SH, Kong IS, Kim DW, Joo WH (2001) Purification and biochemical characterization of a fibrinolytic enzyme from *Bacillus subtilis* BK-17. World J. Microbiol. Biotechnol. 17: 89-92.
Paik et al., 2004: Paik HD, Lee SK, Heo S, Kim SY, Lee H, Kwon TJ (2004) Purification and characterization of the fibrinolytic enzyme produced by *Bacillus subtilis* KCK-7 from Chungkookjang. J. Microbiol. Biotechnol. 14: 829-835.
Kim et al., 1997: Kim HK, Kim GT, Kim DK, Choi WA, Park SH, Jeong YK, Kong IS (1997) Purification and characterization of a novel fibrinolytic enzyme from *Bacillus* sp. KA38 originated from fermented fish. J. Ferment. Bioeng. 84: 307-312.
Jeong et al., 2004: Jeong YK, Kim JH, Gal SW, Kim JE, Park SS, Chung KT, KimYH, KimBW, Joo WH (2004) Molecular cloning and characterization of the gene encoding a fibrinolytic enzyme from *Bacillus subtilis* Strain A1. World J. Microbiol. Biotechnol. 20: 711-717.
Lee et al., 2005: Lee SY, Kim JS, Kim JE, Sapkota K, Shen MH, Kim S, Chun HS, Yoo JC, Choi HS, Kim MK, Kim SJ (2005) Purification and characterization of fibrinolytic enzyme from cultured mycelia of *Armillaria mellea*. Protein Expr. Purif. 43: 10-17.
Lee et al., 2001: Lee SK, Bae DH, Kwon TJ, Lee SB, Lee HH, Park JH, Heo S, Johnson MG (2001) Purification and characterization of a fibrinolytic enzyme from *Bacillus* sp. KDO-13 isolated from soybean paste. J. Microbiol. Biotechnol. 11: 845-852.

*Primary Examiner* — Ganapathirama Raghu
(74) *Attorney, Agent, or Firm* — Chun-Ming Shih (57) ABSTRACT

A *Pseudomonas* sp. strain TKU015 is deposited under DSMZ GmbH (Deutsche Sammlung von Mikroorganismen und Zellkulturen GmbH) Number DSM 21747). The *Pseudomonas* sp. strain TKU015 can be used to produce chitinase, chitosanase and nattokinase. A method of producing chitinase, chitosanase and nattokinases can use the *Pseudomonas* sp. strain TKU015.

12 Claims, 8 Drawing Sheets

FIG. 1

GATCCCCGCTCAGATTGAACGCTGGCGGCAGGCCTAACACATGCAAGTCGAGCGGA
TGACGGGAGCTTNCTCCTTGATTCAGCGGCGGACGGTGAGTAATGCCTAGGAATCT
GCCTGGTAGTGGGGACAACGTTCCGAAAGGAGCGCTAATACCGCATACGTCCTAC
GGGAGAAAGTGGGGGATCTTCGGACCTCACGCTATCAGATGAGCCTAGTCGGATTA
GCTAGTTGGTGAGGTAAAGGCTCACCAAGGCGACGATCCGTAACTGGTCTGAGAGG
ATGATCAGTCACACTGGAACTGAGACACGGTCCAGACTCCTACGGGAGGCAGCAGT
GGGGAATATTGGACAATGGGCGAAAGCCTGATCCAGCCATGCCGCGTGTGTGAAGA
AGGTCTTCGGATTGTAAAGCACTTTAAGTTGGGAGGAAGGGCAGTAAGTTAATACC
TTGCTGTTTTGACGTTCCGACAGAATAACACCGGCTAACTCTGTGCCAGCAGCCGC
GGTAATACAGAGGTGCAAGCGTTATCGGAATTACTGGGCGTAAAGCGCGCGTAGGC
GTTCGTTAAGTTGG

SEQUENCE LISTING

<160> NUMBER OF SEQ ID NOS: 1

<210> SEQ ID NO 1
<211> LENGTH: 574
<212> TYPE: DNA
<213> ORGANISM: Pseudomonas sp.
<220> FEATURE:
<221> NAME/KEY: misc_feature
<222> LOCATION: (69)..(69)
<223> OTHER INFORMATION: n stands for any base

<400> SEQUENCE: 1

```
gatccccgct cagattgaac gctggcggca ggcctaacac atgcaagtcg agcggatgac      60
gggagcttnc tccttgattc agcggcggac ggtgagtaat gcctaggaat ctgcctggta     120
gtgggggaca acgttccgaa aggagcgcta ataccgcata cgtcctacgg gagaaagtgg     180
gggatcttcg gacctcacgc tatcagatga gcctagtcgg attagctagt tggtgaggta     240
aaggctcacc aaggcgacga tccgtaactg gtctgagagg atgatcagtc acactggaac     300
tgagacacgg tccagactcc tacgggaggc agcagtgggg aatattggac aatgggcgaa     360
agcctgatcc agccatgccg cgtgtgtgaa gaaggacttc ggattgtaaa gcactttaag     420
ttgggaggaa gggcagtaag ttaataccttt gctgttttga cgttccgaca gaataacacc     480
ggctaactct gtgccagcag ccgcggtaat acagaggtgc aagcgttatc ggaattactg     540
ggcgtaaagc gcgcgtagtg gttcgttaag ttgg                                   574
```

PSEUDOMONAS SP. STRAIN AND METHOD OF PRODUCING CHITINASE, CHITOSANASE AND NATTOKINASE USING THE SAME

REFERENCE TO SEQUENCE LISTING

A sequence listing is enclosed as an attachment, and the content of the sequence listing information recorded in computer readable form is identical to the written sequence listing.

BACKGROUND

Soybeans don't contain plasmin. Generally, natto is produced by inoculating *Bacillus natto* or *Bacillus subtilis* into braised soybeans and then fermenting the soybeans. A kinase, which names as nattokinase, exists in viscousness distributed on surface of produced natto. Nattokinase acts as a fibrinolytic enzyme of thrombus; therefore, nattokinase is very useful in prevention and curing of brain stroke and myocardial infarction, as well as Alzheimer's disease caused by infarction in small vein.

Plasmin is the only fibrinolytic enzyme contained in human body. Usually, blood contains a plasmin precursor called plasminogen. Fibrinolytic enzyme is a plasminogen activator that can activate plasminogen and thereby producing plasmin. Nattokinase has similar properties of fibrinolytic enzyme; therefore, nattokinase is capable of dissolving fibrin in blood serum. Furthermore, nattokinase reacts with pro-urokinase together with a pro-urokinase activator thereby obtaining urokinase. Urokinase reacts with plasminogen and fibrinolytic enzyme is obtained. The obtained fibrinolytic enzyme further dissolves thrombus and produces thrombus degradation products. In summary, nattokinase can decreases thrombus by increasing amount of fibrinolytic enzyme.

Except in fermented soybean, nattokinase is also found in bacillus, actinomyces, epiphyte and alga. However, there isn't any prior art discloses that nattokinase can be produced from bacteria doesn't belong to pseudomonas sp. and bacillus sp.

Shrimp and crab shell powder (SCSP) contains mass amount of protein and chitin, if SCSP can be fermented with a microorganism to produce valuable bioactive substance, pollution to the environment can be reduced and value in use of SCSP can be improved.

BRIEF SUMMARY

In one exemplary embodiment, a *Pseudomonas* sp. strain TKU015 (gene pool number EU103629, was deposited with DSMZ GmbH (Deutsche Sammlung von Mikroorganismen and Zellkulturen GmbH) as Deposit Number DSM 21747). The *Pseudomonas* sp. strain TKU015 can be used to produce chitinase, chitosanase and nattokinases.

In another exemplary embodiment, a method of producing nattokinase is provided. The method utilizes the *Pseudomonas* sp. strain TKU015 to ferment a solution of aquatic products castoff powder and nattokinases is thereby obtained. Pollution of the aquatic products to environment is reduced and value of the aquatic products is improved.

The strain TKU015 is selected from soil in North Taiwan and cultured using shrimp shell powder as unique carbon/nitrogen source. Identification results show that TKU015 belongs to *Pseudomonas* sp.

Nattokinase can be produced by fermenting a solution of aquatic products castoff powder using the *Pseudomonas* sp. strain TKU015. The aquatic products castoff comprises shrimp and crab shell, squid pen powder, mushroom and crude chitin. A concentration range of the aquatic products castoff powder is 0.1%-3%, preferably, the range is 0.2-1.5%.

Generally, culture medium that is suitable for producing chitinase and chitosanase includes 0.5% by weight of shrimp shell powder (SSP), 0.1% by weight of $K_2HPO_4$, and 0.05% by weight of $MgSO_4 \cdot 7H_2O$. The *Pseudomonas* sp. strain TKU015 is cultured in the medium (pH 8) for 3 days at 30° C. The obtained fermented supernatant is processed with Ammonium sulfate precipitation, DEAE-Sepharose chromatography, Phenyl-Sepharose chromatography and Sephacryl S-100 chromatography, and then chitinase and chitosanase is separated. SDS-PAGE testing results show that molecular weight of chitinase and chitosanase is 68 kDa and 30 kDa respectively. Optimum reacting pH value, optimum reacting temperature, pH stable range, thermal stable range of chitinase are pH 5, 50° C., pH 5-7, and <60° C.; optimum reacting pH value, optimum reacting temperature, pH stable range, thermal stable range of chitosanase are pH 4, 50° C., pH 3-9, and <50° C. Activity of chitinase is inhibited by $Mn^{2+}$ and $Fe^{2+}$, activity of chitosanase is inhibited by $Mn^{2+}$, $Cu^{2+}$ and PMSF.

Generally, culture medium that is suitable for producing chitinase and chitosanase includes 0.2-1.5% by weight of shrimp shell powder (SSP), 0.05-0.2% by weight of $K_2HPO_4$, and 0.02-0.1% by weight of $MgSO_4 \cdot 7H_2O$. Preferably, the culture medium includes 1% by weight of shrimp shell powder (SSP), 0.1% by weight of $K_2HPO_4$, and 0.05% by weight of $MgSO_4 \cdot 7H_2O$. The *Pseudomonas* sp. strain TKU015 is cultured in the medium (pH 7) for 2 days at 30° C. The obtained fermented supernatant is processed with Ammonium sulfate precipitation, DEAE-Sepharose chromatography, and Phenyl-Sepharose chromatography, and then nattokinase is separated. SDS-PAGE testing results show that molecular weight of nattokinase is 21 kDa and 30 kDa respectively. Optimum reacting temperature, pH stable range, thermal stable range of nattokinase are pH 7, 50° C., pH 4-11, and <37° C. Activity of nattokinase is completely inhibited by PMSF. $Fe^{2+}$ can improve activity of nattokinases.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Culture of New Strain TKU015

An amount of pre-gathered soil is dissolved in an appropriate amount of germfree water and the obtained solution is coated on a solid culture medium comprising 1% by weight of shrimp shell powder (SSP), 0.1% by weight of $K_2HPO_4$, 0.05% by weight of $MgSO_4 \cdot 7H_2O$ and 1.5% by weight of agar. The medium is cultured for two days at 30° C., and the colony is observed. Produced single colony is inoculated into a nutrient agar (NA) medium and cultured for one day at 30° C. After that, the NA medium is stored at 4° C. Single colony filtrated from the NA medium is cultured in 100 mL liquid medium disposed in a 250 mL conical flask for two days at 30° C. using a shaking culture method. The liquid medium includes 1% by weight of SSP, 0.1% by weight of $K_2HPO_4$, and 0.05% by weight of $MgSO_4 \cdot 7H_2O$ disposed. Finally, the liquid medium is centrifugally purified, supernatant is separated, and activity of chitinase and chitosanase of the supernatant is tested.

Characteristics of TKU015 Strain

Figure 1:
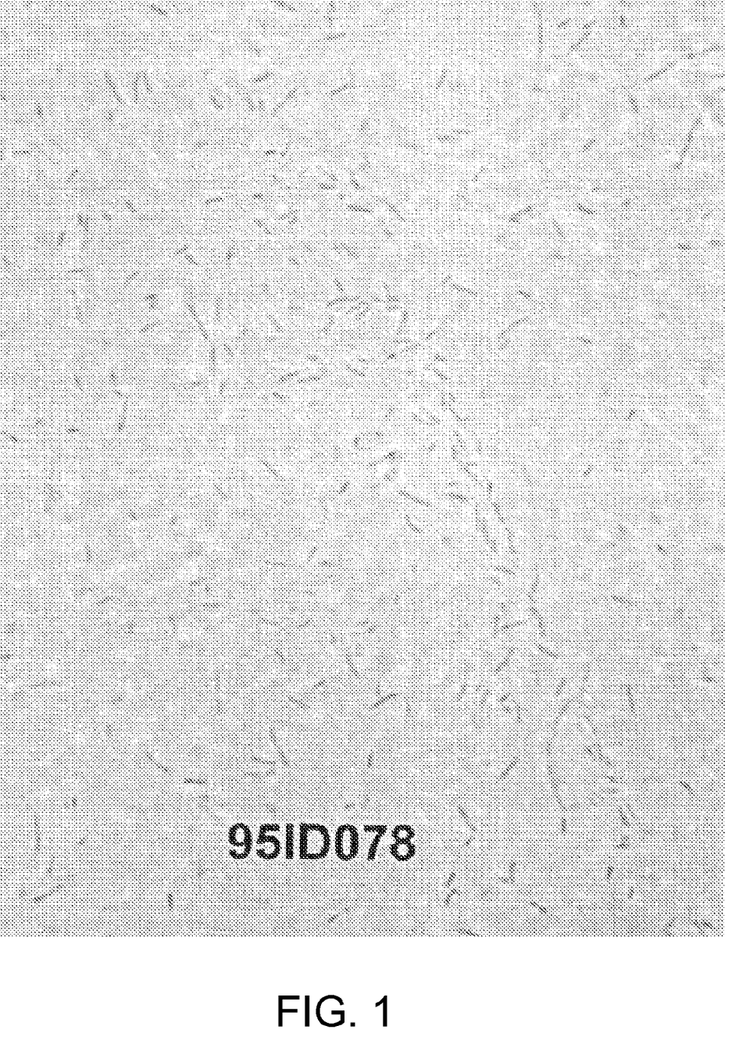
FIG. 1 is a microscope photograph of a *Pseudomonas* sp. strain TKU015 provided in an embodiment of the present invention.

As shown in FIG. 1, TKU015 is one kind of Gram-negative, which has catalase, oxidase and motility, and can grow both in an aerobic and an anaerobic environment, but does not produce spores.

Figure 2:
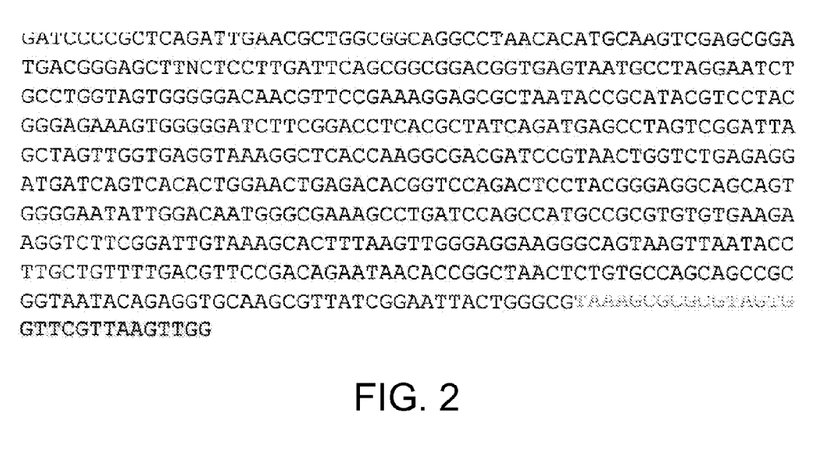
FIG. 2 is a partial 16S rDNA nucleic acid sequence of *Pseudomonas* sp. strain TKU015 (SEQ ID NO: 1)

FIG. 2 illustrates a portion of 16 S rDNA nucleotide sequence analysis result, which indicates that TKU015 is most close to *Pseudomonas* sp. and similarity of TKU015 and *Pseudomonas* sp. exceeds 97%.

Testing result of glucose metabolism type indicates that TKU015 is oxidized type and is consistent with characteristics of *Pseudomonas* sp.

Analysis of fatty acid composition indicates that main fatty acid composition of TKU015 includes C16:0 and H18:1ω7c, hydroxylated fatty acids C10:0 3OH, C12:0 2OH and C12:0 3OH can also be found in TKU015, but TKU015 doesn't contain C16:0 2OH and C16:0 3OH. The fatty acid composition is also consistent with *Pseudomonas* sp.

Preparation of Chitin

In step a, squid pen powder (SPP) is mixed with a 2N NaOH solution in a ratio of 3:40 (w/v), the obtained mixture is heated in a 100° C. hot water bath for 30 minutes, residual and filtrate are separated by filtrating, the residual is dried at 60° C. and then weighted. The dried residual is mixed with a 2N HCl solution in a ration of 1:8 (w/v). The residual is soaked fort two days at room temperature. Residual and filtrate are separated by filtrating, the residual is dried at 60° C. and then weighted.

In step b, 5 g residual is added into 50 mL of 12N HCl solution and then stirred for 1 hour, the obtained mixture is poured into distilled water, supernatant liquor is removed precipitation, and the residual is washed with 50 mL $H_3PO_4$ (pH 7), the washing step is repeated until pH value of supernatant equals to 7. After the supernatant is removed, the obtained sediment is chitin suspension, which can be stored at 4° C. for testing its activity of chitinase.

In order to produce chitinase and chitosanase, generally, TKU015 is cultured in a liquid shaking culture medium (pH 8) including 0.5% by weight of SSP, 0.1% by weight of $K_2HPO_4$ and 0.05% by weight of $MgSO_4 \cdot 7H2O$ for 3 days at 30° C. The obtained fermented supernatant is purified with ammonia sulfate precipitation, DEAE-Sepharose chromatography, Phenyl-Sepharose chromatography, and Sephacryl S-100 chromatography in sequence, and a chitinase and a chitosanase is obtained. Testing result of Sodium Dodecyl Sulfate-Polyacrylamide Gel Electrophoresis (SDS-PAGE) indicates that the chitinase has a molecular weight of 68 kDa and the chitosanase has a molecular weight of 30 kDa. An optimum pH value and an optimum temperature for producing chitinase are pH 5 and 50° C., and chitinase is stable under pH 5-7 and a temperature less than 60° C. An optimum pH value and an optimum temperature for producing chitosanase are pH 4 and 50° C., and chitinase is stable under pH 3-9 and a temperature less than 50° C. Activity of chitinase can be prohibited by $Mn^{2+}$ and $Fe^{2+}$, and activity of chitosanase can be inhibited by $Mn^{2+}$, $Cu^{2+}$, and phenylmethanesulfonyl fluoride (PMSF).

Activity Test of Nattokinase

Protease activity of the supernatant obtained from culture medium of chitinase (cultured in a liquid shaking culture medium (pH 8) including 0.5% by weight of SSP, 0.1% by weight of $K_2HPO_4$ and 0.05% by weight of $MgSO_4 \cdot 7H_2O$ for 3 days at 30° C.) is respectively tested using casein and N-succinyl-Ala-Ala-Pro-Phe-pNa as substrate. The supernatant hasn't protease activity when casein is employed as substrate. In contrast, the supernatant has protease activity when N-succinyl-Ala-Ala-Pro-Phe-pNa is employed as substrate; this indicates that the supernatant has nattokinase activity (0.02 FU/mL). In summary, the supernatant contains chitinase, chitosanase and nattokinase.

Selection of Carbon/Nitrogen Source

Figure 3:
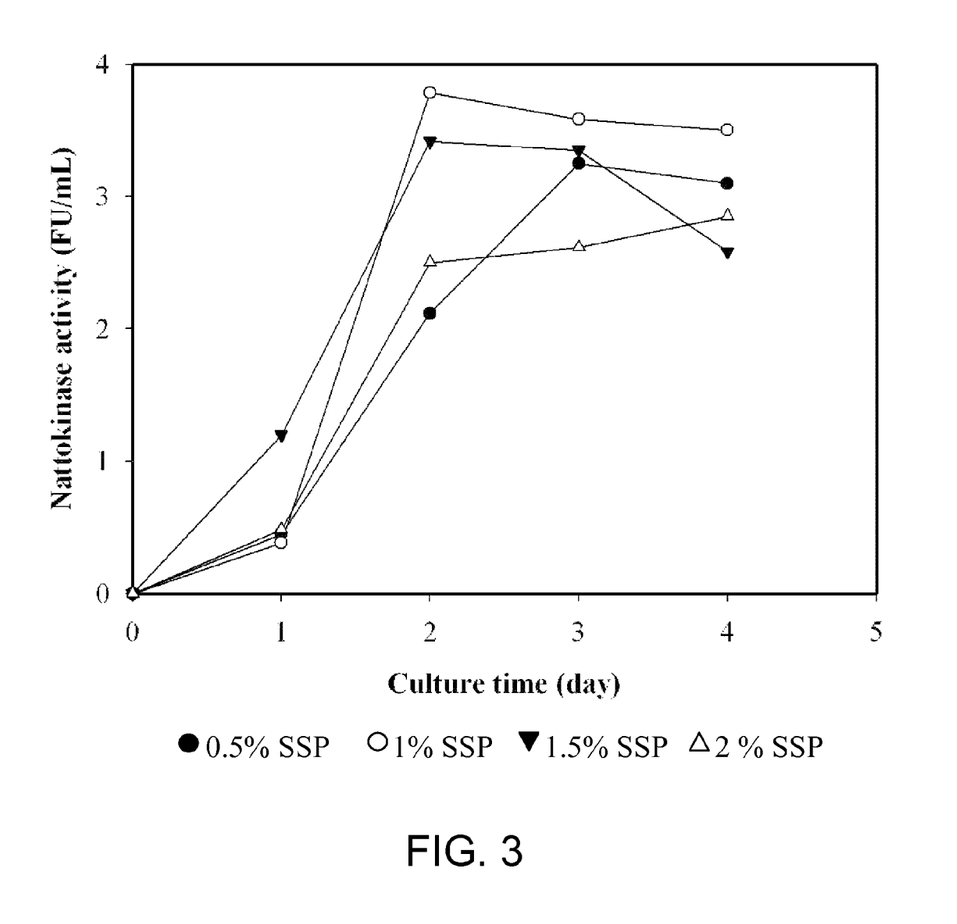
FIG. 3 is a graph showing influence of concentration of SSP to produced nattokinases activity.

Chitosanase and nattokinase also exist in supernatant obtained from culture medium that is cultured under an appropriate environment for producing chitinase. In order to maximize output of nattokinase, SSP is employed as main carbon source of nattokinase. In addition, other condition of producing nattokinase is also discussed. Preferably, a concentration of SSP is 1% by weigh (3.8 FU/mL) (referring to FIG. 3).

Appropriate Condition for Producing Nattokinase

Figure 4:
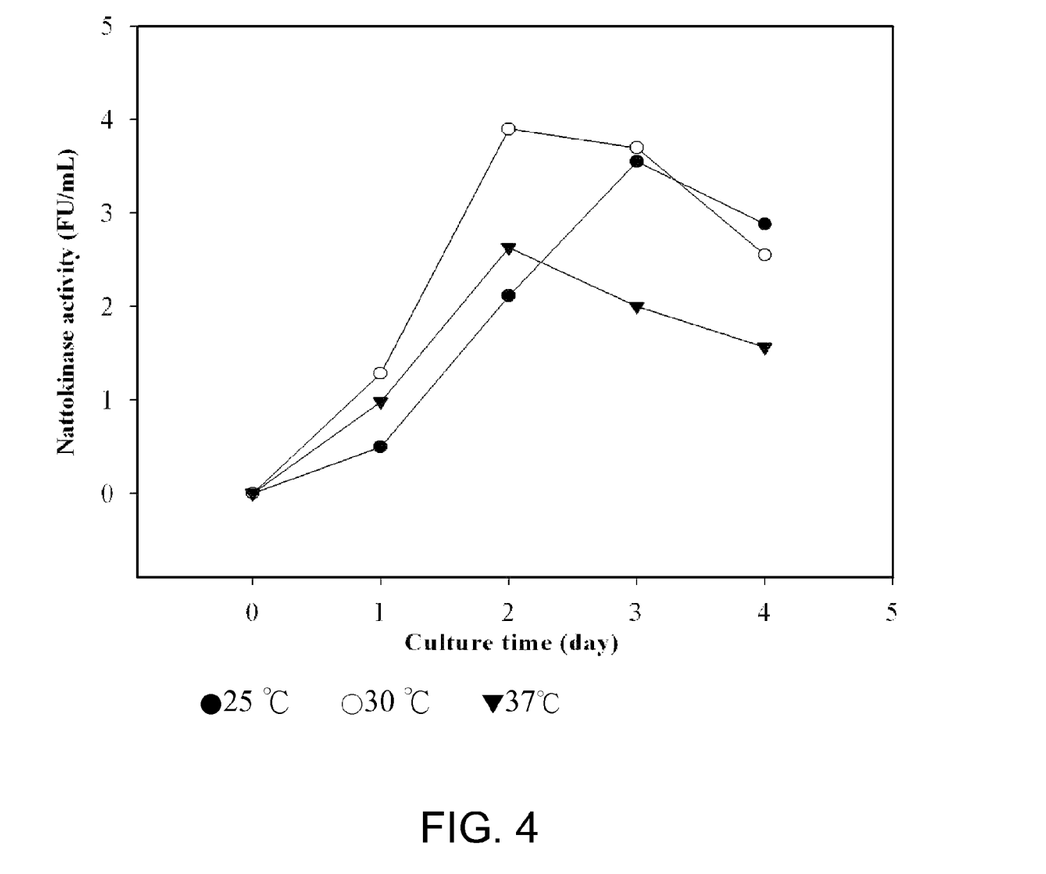
FIG. 4 is a graph showing influence of temperature to produced nattokinases activity.

As described above, appropriate carbon source for producing nattokinase is 1% SSP. The carbon source is cultured under different temperature (25° C., 30° C., 37° C.) for 1-4 days. The nattokinase activity testing results are shown in FIG. 4, when cultured for 2 days at 30° C., a highest nattokinase activity (4 FU/mL) is obtained. 30° C. is most appropriate temperature for producing nattokinase.

Figure 5:
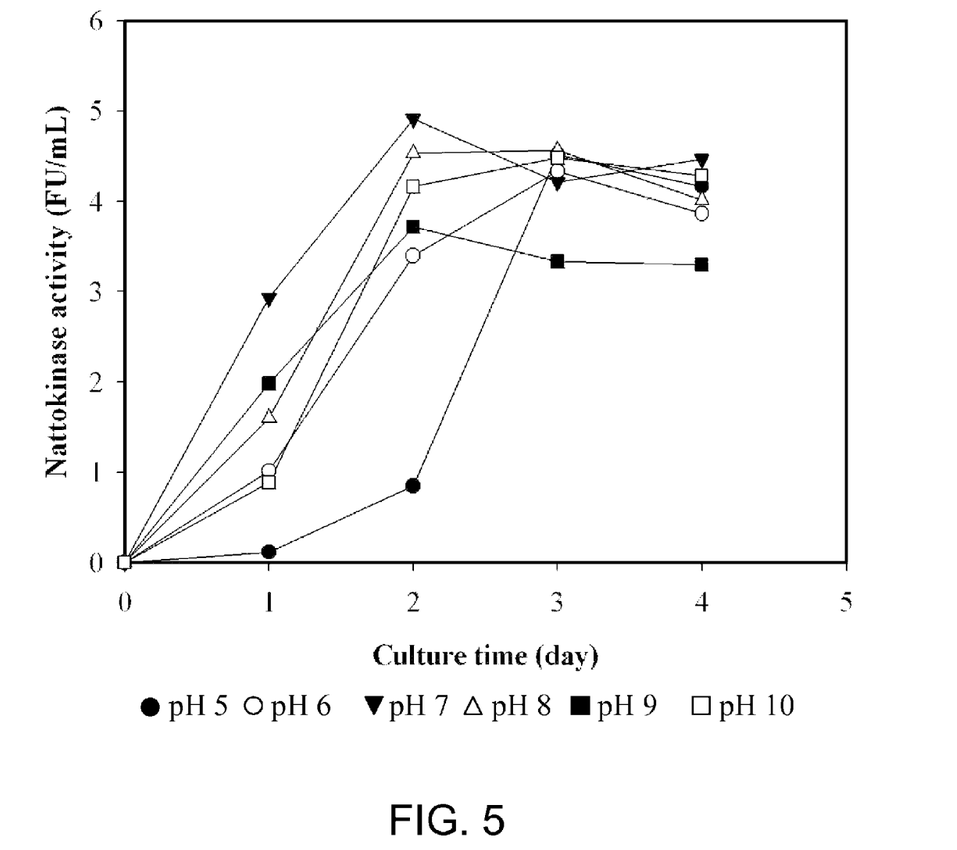
FIG. 5 is a graph showing influence of pH value to produced nattokinases activity.

Culture mediums have different pH values (5-10) is cultured for 1-4 days at 30° C., and nattokinase activity testing results are shown in FIG. 5, when the pH value of culture medium is 7 a highest nattokinase activity (4 FU/mL) is obtained.

Figure 6:
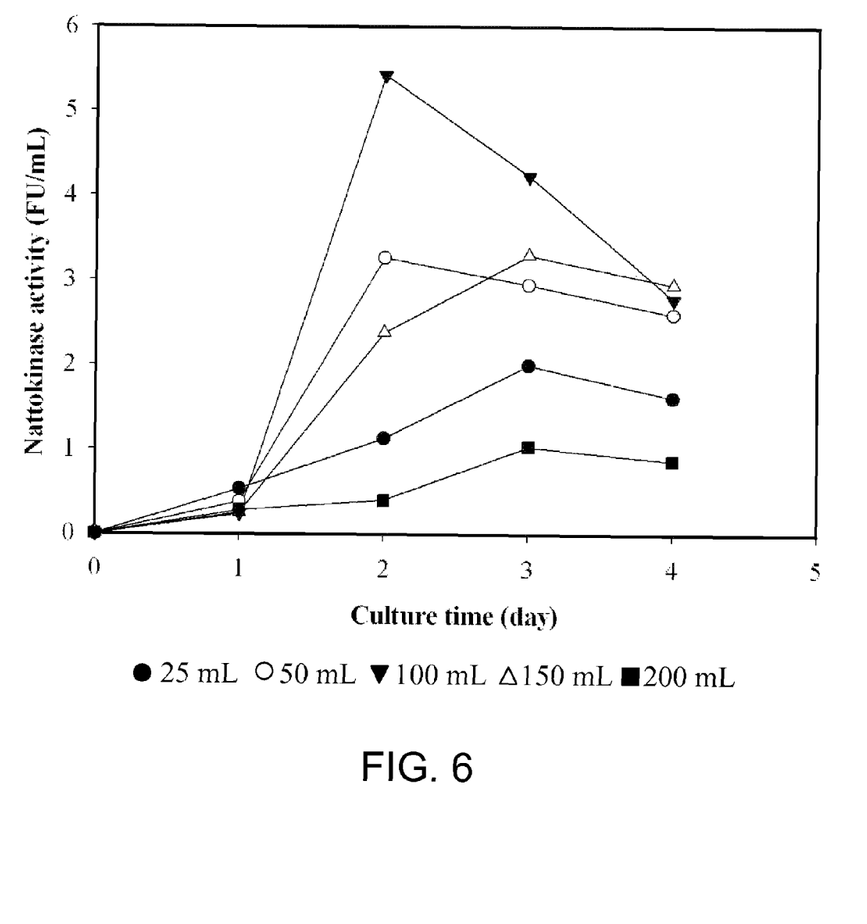
FIG. 6 is a graph showing influence of volume of culture medium to produced nattokinases activity.

Different volumes (50 mL, 100 mL, 150 mL, and 200 mL) of culture medium, which contains 1% SSP and has a pH value of 8, is disposed in a 250 conical flask and cultured for 1-4 days at 30° C. nattokinase activity testing results are shown in FIG. 6, when the volume of culture medium is 100 mL a highest nattokinase activity (5.5 FU/mL) is obtained.

In summary, optimum conditions for producing nattokinase include: 100 mL shaking culture medium (pH 7) including 1% by weight of SSP, 0.1% by weight of $K_2PO_4$ and 0.05% by weight of $MgSO_4 \cdot 7H2O$ cultured for 2 days at 30° C., which can result in a highest nattokinase activity.

Figure 7:
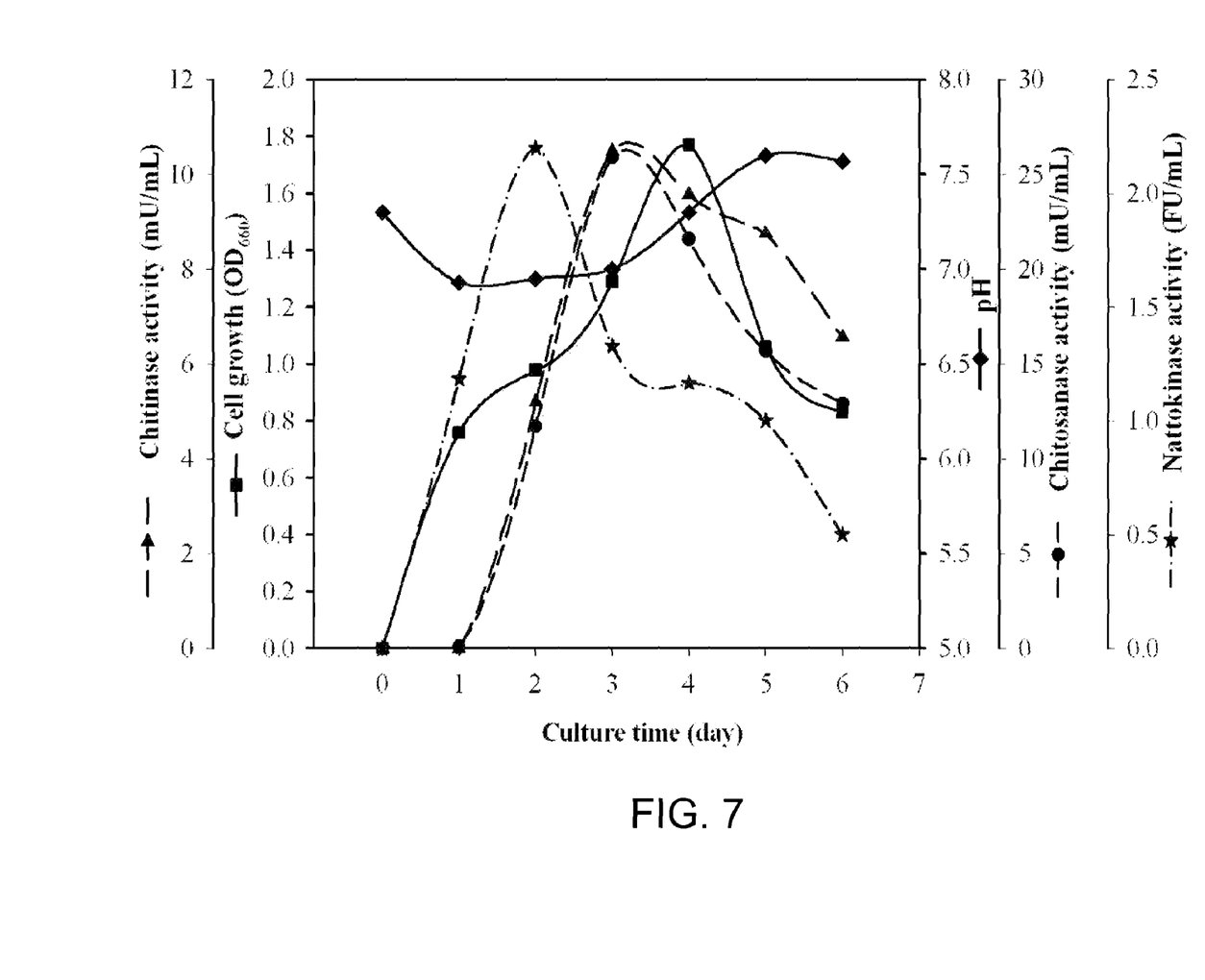
FIG. 7 is a graph showing growth curves of chitinase, chitosanase and nattokinases produced in a culture medium of *Pseudomonas* sp. strain TKU015.

FIG. 7 illustrates a growth curve of *Pseudomonas* sp. TKU015 cultured in a shaking liquid medium (pH 8) including 0.5% by weight of SSP, 0.1% by weight of $K_2HPO_4$, and 0.05% by weight of $MgSO_4 \cdot 7H2O$ at 30° C. It is known that nattokinase activity is highest on the second day, and then nattokinase activity decreases with increasing of time. The chitinase and chitosanase activity is highest on the third day.

Separating and Purifying of Nattokinase

Crude enzyme extract preparation: TKU015 is cultured in an appropriate culture medium; the obtained fermentation broth is processed with ammonium sulfate precipitation and centrifugal separation; remained sediments are re-dissolved with a few 50 mM phosphate buffer solution (pH 7) and then dialyze at 4° C.; the resulted dialysis fluid is crude enzyme extract (50 mL).

Anion exchange chromatography: the crude enzyme extract is injected into a column for performing DEAE-Sepharose CL-6B column chromatography, a flow rate of the crude enzyme extract is 4 mL/min, every 6 mL of resulted solution is collected in a cuvette, non-adsorbed protein is collected, and then the column is eluted with 50 mM phosphate buffer solution (pH 7) that contain NaCl at a gradient of 0-1 M such that adsorbed protein is eluted out; nattokinase is found in non-adsorbed area and is collected as nattokinase solution (100 mL).

Hydrophobic chromatography: 80 mL of nattokinase solution (containing 1 M ammonium sulfate) is injected into a Phenyl Sepharose 6 Fast Flow column, a flow rate of the nattokinase solution is 4 mL/min, each 6 mL of resulted solution is collected in a cuvette; firstly, the column is eluted with 50 mM phosphate buffer solution (pH 7) that contain 1 M ammonium sulfate; and then the column is eluted with different 50 mM phosphate buffer solution (pH 7) that contain from 1 M to 0 M of NaCl to change hydrophobicity of the column, the nattokinase solution can be separated under at different hydrophobicity. Finally, the column is eluted with 50 mM phosphate buffer solution (pH 7) to wash hydrophobic protein out of the column. Area having nattokinase activity is collected (70 mL) and enzyme characteristics analysis and SDS-PAGE is performed.

Comprehensive Results: during the purification process, nattokinase exists in non-adsorbed area of the DEAE-Sepharose column, after the followed hydrophobic Phenyl-Sepharose chromatography step, TKU015 nattokinase (45 mg) can be separated. DEAE-Sepharose separation results at pH 7 show that chitosan and nattokinase both exists in non-adsorbed area and isoelectric points of both should belong to alkaline pH.

DEAE-Sepharose separation results show that chitosan appears after the solvent gradient is increased; therefore, chitosan should be a hydrophobic protein. In contrast, nattokinase appears prior to the solvent gradient is increased; therefore, nattokinase should be a hydrophilic protein. Purification ration of nattokinase is 5.1.

The Molecular Weight Determination of Nattokinase

Figure 8:
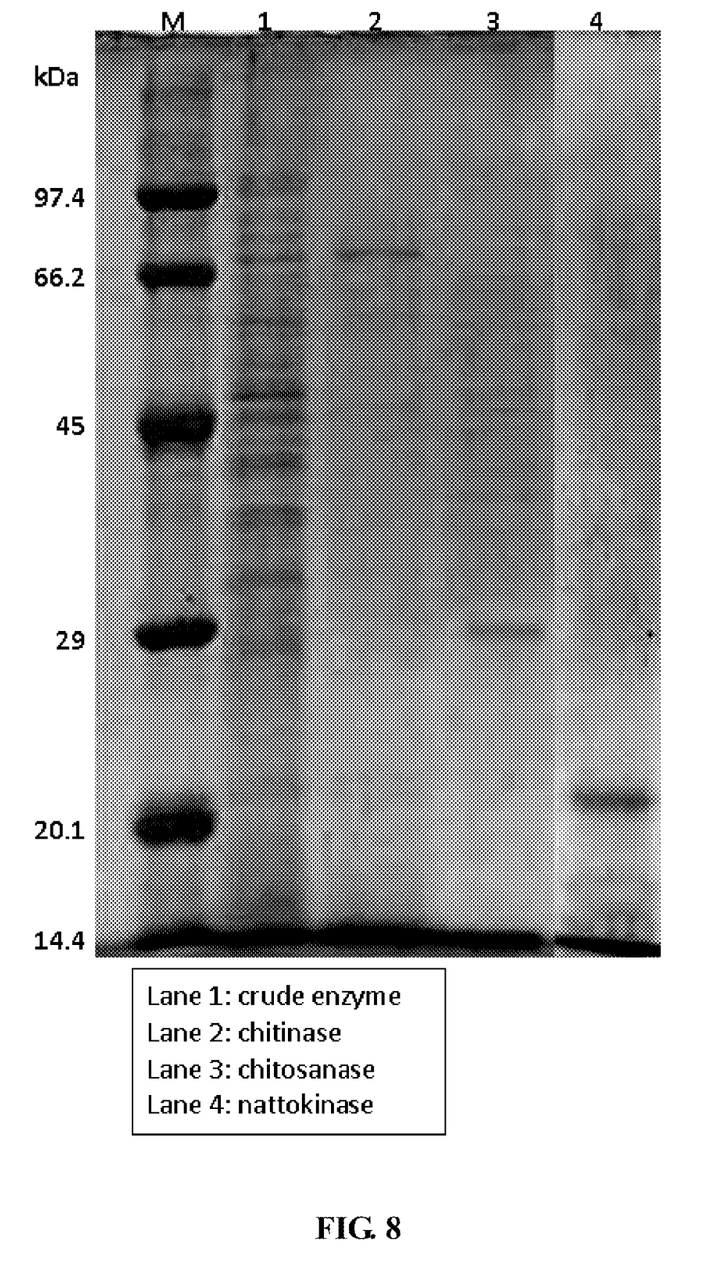
FIG. 8 is SDS-PAGE analysis graph of chitosanase and nattokinases produced by *Pseudomonas* sp. strain TKU015.

SDS-PAGE: molecular weight of nattokinase is analyzed using 12.5% SDS-PAGE, and testing result is shown in FIG. 8, in which Lane 1 belongs to crude enzyme extract and Lane 4 belongs to TKU015 nattokinase. Molecular weight of nattokinase is about 21 kDa.

Comprehensive Results: molecular weight of TKU015 nattokinase is about 21 kDa, as shown in Table 1, molecular weight of majority of nattokinase that are produced from microorganisms are in a range from 20 kDa to 45 kDa. Currently, it is not found that *Pseudomonas* is used in production of nattokinase. Molecular weight of TKU015 nattokinase is less than that of nattokinase produced by bacteria, and is similar to that of nattokinase produced by fungi such as *Armillaria mellea* AMMP (21 kDa) and *Rhizopus chinensis*. 12(18 kDa). As shown in Table 1, majority of nattokinase are produced by bacteria and fungi. Molecular weight of nattokinase produced from bacteria is about 30 kDa, and nattokinase produced from the *Pseudomonas* sp. TKU015 is similar to that of fungi.

TABLE 1

Properties comparison of nattokinase produced by different microorganisms

| Source | Molecular mass (kDa) | Optimum pH | Optimum temp (° C.) | Type of protease | Reference |
| --- | --- | --- | --- | --- | --- |
| *Pseudomonas* sp. TKU015 | 21 | 7 | 50 | Serine | |
| *Streptomyces* spp. SW-1 | 30 | 8 | | Serine and Metallo | Wang et al., 1999 |
| *Rhizopus chinensis*. 12 | 18 | 10.5 | 45 | | Xiao-Lan et al., 2005 |
| *Bacillus natto* nattokinase | 27.7 | | | Serine | Fujita et al., 1993 |
| *Bacillus amyloliquefaciens* DC-4 | 28 | 9 | 48 | Serine | Peng et al., 2003 |
| *Bacillus subtilis* CK | 28.2 | 10 | 70 | Serine | Kim et al., 1996 |
| *Bacillus* sp. subtilisin DJ-4 | 29 | 10 | 40 | Serine | Kim and Choi, 2000 |
| *Bacillus* sp. subtilisin QK-2 | 28 | 8.5 | 55 | Serine | Ko et al., 2004 |
| *Bacillus subtilis* BK-17 | 31 | | | Metallo | Jeong et al., 2001 |
| *Bacillus subtilis* KCK-7 | 44 | 8 | 50 | Serine | Paik et al., 2004 |
| *Bacillus* sp. KA38 | 41 | 7 | 40 | Metallo | Kim et al., 1997 |
| *Bacillus subtilis* strain A1 | 31.4 | 7 | 50 | Metallo | Jeong et al., 2004 |

TABLE 1-continued

Properties comparison of nattokinase produced by different microorganisms

| Source | Molecular mass (kDa) | Optimum pH | Optimum temp (° C.) | Type of protease | Reference |
|---|---|---|---|---|---|
| *Armillaria mellea* AMMP | 21 | 6 | 33 | Metallo | Lee et al., 2005 |
| *Bacillus* sp. KDO-13 | 45 | 7 | 60 | Metallo | Lee et al., 2001 |

The references cited in Table 1 are listed in detail:
1. Wang et al., 1999: Wang J, Wang M, Wang Y (1999) Purification and characterization of a novel fibrinolytic enzyme from *Streptomyces* spp. Chin. *J. Biotechnol.* 15: 83-89.
2. Xiao-Lan et al., 2005: Liu X L, Du L X, Lu F P, Zheng X Q, Xiao J. (2005) Purification and characterization of a novel fibrinolytic enzyme from *Rhizopus chinensis* 12, *Appl. Microbiol. Biotechnol.* 67: 209-214.
3. Fujita et al., 1993: Fujita M, Nomura K, Hong K, Ito Y, Asada A, Nishimuro S (1993) Purification and characterization of a strong fibrinolytic enzyme (Nattokinase) in the vegetable cheese natto, a popular soybean fermented food in Japan. *Biochem Biophys. Res. Commun.* 197: 1340-1347.
4. Peng et al., 2003: Peng Y, Huang Q, Zhang R H, Zhang Y Z (2003) Purification and characterization of a fibrinolytic enzyme produced by *Bacillus amyloliquefaciens* DC-4 screened from douchi, a traditional Chinese soybean food. Comp. Biochem. Physiol. *Biochem. Mol. Biol.* 134: 45-52.
5. Kim et al., 1996: Kim W, Choi K, Kim Y, Park H, Choi J, Lee Y, Oh H, Kwon I, Lee S (1996) Purification and characterization of a fibrinolytic enzyme produced from *Bacillus* sp. strain CK 11-4 screened from Chungkook-Jang. *Appl. Environ. Microbiol.* 62: 2482-2488.
6. Kim and Choi, 2000: Kim S H, Choi N S (2000) Purification and characterization of subtilisin DJ-4 secreted by *Bacillus* sp. strain DJ-4 screened from Doen-Jang. *Biosci. Biotechnol. Biochem.* 64: 1722-1725.
7. Ko et al., 2004: Ko J H, Yan J P, Zhu L, Qi Y P (2004) Identification of two novel fibrinolytic enzymes from *Bacillus subtilis* QK02. Comp. *Biochem. Physiol. C Toxicol.* Pharmacol. 137: 65-74.
8. Jeong et al., 2001: Jeong Y K, Park J U, BaekH, Park S H, Kong I S, Kim D W, Joo W H (2001) Purification and biochemical characterization of a fibrinolytic enzyme from *Bacillus subtilis* BK-17. *World J. Microbiol Biotechnol.* 17: 89-92.
9. Paik et al., 2004: Paik H D, Lee S K, Heo S, Kim S Y, Lee H, Kwon T J (2004) Purification and characterization of the fibrinolytic enzyme produced by *Bacillus subtilis* KCK-7 from Chungkookjang. *J. Microbiol. Biotechnol.* 14: 829-835.
10. Kim et al., 1997: Kim H K, Kim G T, Kim D K, Choi W A, Park S H, Jeong Y K, Kong I S (1997) Purification and characterization of a novel fibrinolytic enzyme from *Bacillus* sp. KA38 originated from fermented fish. *J. Ferment. Bioeng.* 84: 307-312.
11. Jeong et al., 2004: Jeong Y K, Kim J H, Gal S W, Kim J E, Park S S, Chung K T, Kim Y H, Kim B W, Joo W H (2004) Molecular cloning and characterization of the gene encoding a fibrinolytic enzyme from *Bacillus subtilis* Strain A1. *World J. Microbiol. Biotechnol.* 20: 711-717.
12. Lee et al., 2005: Lee S Y, Kim J S, Kim J E, Sapkota K, Shen M H, Kim S, Chun H S, Yoo J C, Choi H S, Kim M K, Kim S J (2005) Purification and characterization of fibrinolytic enzyme from cultured mycelia of *Armillaria mellea*. Protein *Expr. Purif.* 43: 10-17.
13. Lee et al., 2001: Lee S K, Bae D H, Kwon T J, Lee S B, Lee H H, Park J H, Heo S, Johnson M G (2001) Purification and characterization of a fibrinolytic enzyme from *Bacillus* sp. KDO-13 isolated from soybean paste. *J. Microbiol. Biotechnol.* 11: 845-852.

Analysis of the Characteristics of Nattokinase

Optimum temperature and thermal stability range of TKU015 nattokinase are 50° C. and <37° C. As shown in table 1, most optimum temperature and thermal stability range of nattokinase are 37-50° C. and <50° C. With respect to optimum temperature, nattokinases produced by bacteria of *Bacillus subtilis* KCK-7 (50° C., *Bacillus subtilis* Strain A1 (50° C.) and *Bacillus amyloliquefaciens* DC-4 (48° C.) are similar to TKU015 nattokinase. With respect to thermal stability range, TKU015 nattokinase is relatively non-stable to heat, nattokinase produced by fungi such as *Rhizopus chinensis*. 12 (<37° C.), *Fomitella fraxinea* FFP2 (<40° C.), (Park et al, 2005) is similar to TKU015 nattokinase. Above results indicate that molecular weight and temperature characteristics of *Pseudomonas* sp. TKU015 nattokinase are similar to that of fungi nattokinase.

Optimum pH value and pH stability range of TKU015 nattokinase are pH 7 and pH 4-11. As shown in Table 1, most optimum pH values of nattokinase are in a range from neutral to a little alkaline, and pH stability range are pH 7-10. With respect to optimum pH value, nattokinases produced by *Bacillus* sp. KA38 (pH 7), *Bacillus* sp. KDO-13 (pH 7), and *Bacillus subtilis* Strain A1 (pH 7) are similar to TKU015 nattokinase. With respect to pH stability range, TKU015 nattokinase is stable in a weakly acidic or a weakly alkaline environment, and can remain 80% of activity in a solution having a pH value of 11, nattokinases produced by *Bacillus amyloliquefaciens* DC-4 (pH 4-11) and *Bacillus* sp. *subtilisin* QK-2 (pH 3-12) are similar to TKU015 nattokinase.

Table 2 shows that purified TKU015 nattokinase, which belongs to serine-type protease, is completely inhibited by PMSF, and $Fe^{2+}$ can increase its activity. As shown in table 1, nattokinase produced by *Bacillus amyloliquefaciens* DC-4, *Bacillus* sp. Strain DJ-4, *Bacillus subtilis* QK-2, *Bacillus subtilis* KCK-7, *Bacillus natto* NK (Fujita et al., 1993) and *Bacillus subtilis* DC33 (Wang et al, 2006) are inhibited by PMSF. When the concentration of $Fe^{2+}$ is 5 mM, nattokinase activity is increased to 232% of the original activity, nattokinase shows increased activity when $Ca^{2+}$, $Cu^{2+}$ or $Mg^{2+}$ is added (Peng et al, 2005); $Fe^{2+}$ can influence TKU015 nattokinase activity, however $Ca^{2+}$, $Cu^{2+}$ or $Mg^{2+}$ does not.

TABLE 2

Influence of metal ions on TKU015 nattokinase activity

| Metal ions | Concentration (mM) | Relative activity (%) Nattokinase |
|---|---|---|
| None | 0 | 100 |
| $Mg^{2+}$ | 5 | 104 |
| $Cu^{2+}$ | 5 | 95 |
| $Fe^{2+}$ | 5 | 232 |
|  | 10 | 156 |
| $Mn^{2+}$ | 5 | 102 |
| $Zn^{2+}$ | 5 | 94 |
| $Ba^{2+}$ | 5 | 109 |
| $Ca^{2+}$ | 5 | 108 |
| $Al^{3+}$ | 5 | 101 |
| EDTA | 5 | 117 |
| PMSF | 5 | 45 |
|  | 10 | 0 |

Relative activity 100% represents 19 FU/mL

Table 3 shows influence of different surfactants at different concentration on TKU015 nattokinase activity. When concentration of SDS is 0.5, 1, or 2 mM, TKU015 nattokinase remains 50% activity; when concentration of Triton X-100 is 0.5%, 1%, 2% (v/v), TKU015 nattokinase activity is respectively increased to 160%, 206%, 344% of original activity. In comparison, when concentration of SDS is 0.1%, *Pseudomonas aeruginosa* PseA protease remains 61% activity; and when concentration of Triton X-100 is 0.1% or 0.5%, *Pseudomonas aeruginosa* PseA protease activity doesn't change (Khare et al., 2005).

TABLE 3

Influence of surfactants on TKU015 nattokinase activity

| Surfactant | Concentration | Relative activity (%) Nattokinase |
|---|---|---|
| None | 0 | 100 |
| SDS | 0.5(mM) | 66 |
|  | 1 | 56 |
|  | 2 | 56 |
| Tween 20 | 0.5(%) | 76 |
|  | 1 | 70 |
|  | 2 | 85 |
| Tween 40 | 0.5(%) | 94 |
|  | 1 | 70 |
|  | 2 | 82 |
| Triton X-100 | 0.5(%) | 160 |
|  | 1 | 206 |
|  | 2 | 344 |

Relative activity 100% represents 18 FU/mL

Table 4 shows influence of different organic solvents on TKU015 nattokinase activity. TKU015 nattokinase activity increase to 150% in the presence of acetone; methanol, toluene and xylene do not affect TKU015 nattokinase activity; ether inhibits 50% of TKU015 nattokinase activity; and TKU015 nattokinase remain about 70% of activity in the other solvents. With respect to *Pseudomonas* protease, activity of *Pseudomonas aeruginosa* PseA, (Khare et al., 2005) doesn't change in the presence of toluene and N,N-dimethylformamide (DMF); activity of *Pseudomonas aeruginosa* PST-01, (Ogino et al., 1999) doesn't change in the presence of toluene, DMF and actone; activity of *Pseudomonas aeruginosa* san-ai strain, (Lee et al., 2006) doesn't change in the presence of DMF. Similar to PseA protease, PST-01 protease and san-ai protease, TKU015 nattokinase remains 80% of activity in the presence of DMF. In addition, activity of TKU015 nattokinase and PST-01 protease respectively increased to 150% and 200% in the presence of acetone. With respect to thermal stability, TKU015 nattokinase is mixed with different solvents and then respectively placed for ten days at 25° C. and 4° C. As shown in Table 5, the solvents don't affect activity of nattokinase at 25° C. and 4° C. Similarly, the same effects are also found in *Pseudomonas* sp. PseA protease (Khare et al., 2005) and *Pseudomonas* san-ai protease (Lee et al., 2006).

TABLE 4

Influence of organic solvents on activity of TKU015 nattokinase

| Organic solvents | Relative activity(%) TKU015 nattokinase |
|---|---|
| None | 100 |
| methanol | 96 |
| ethanol | 65 |
| ethyl ether | 43 |
| toluene | 106 |
| ethyl acetate | 70 |
| acetonitrile | 88 |
| acetone | 150 |
| butanol | 70 |
| isoamylalcohol | 60 |
| isopropylalcohol | 68 |
| hexane | 66 |
| xylene | 96 |
| DMSO | 80 |
| DMF | 64 |

Relative activity 100% represents 20 FU/mL

TABLE 5

Influence of organic solvents on TKU015 nattokinase activity at different temperature

| Organic solvent | Temperature (° C.) | Relative activity(%) TKU015 nattokinase |
|---|---|---|
| None | 25 | 100 |
|  | 4 | 100 |
| methanol | 25 | 90 |
|  | 4 | 116 |
| ethanol | 25 | 88 |
|  | 4 | 114 |
| ethyl ether | 25 | 70 |
|  | 4 | 98 |
| toluene | 25 | 100 |
|  | 4 | 120 |
| ethyl acetate | 25 | 92 |
|  | 4 | 118 |
| acetonitrile | 25 | 80 |
|  | 4 | 90 |
| acetone | 25 | 108 |
|  | 4 | 128 |
| butanol | 25 | 85 |
|  | 4 | 125 |
| isoamylalcohol | 25 | 100 |
|  | 4 | 88 |
| isopropylalcohol | 25 | 120 |
|  | 4 | 115 |
| xylene | 25 | 96 |
|  | 4 | 126 |
| DMSO | 25 | 94 |
|  | 4 | 90 |
| DMF | 25 | 98 |
|  | 4 | 120 |

Relative activity 100% represents 15 FU/mL

*Pseudomonas* sp. TKU015 is cultured in a liquid medium (100 mL/250 mL), which employ shrimp shell powder as carbon/nitrogen source, for 2-3 days at 30° C., and chitinase, chitosanase and nattokinase activity are tested in the medium. The fermented supernatant is processed by Ammonium sulfate precipitation, DEAE-Sepharose chromatography, Phenyl-Sepharose chromatography and Sephacryl S-100 chromatography, and then three pure enzymes (chitinase, chitosanase and nattokinase) are obtained. Test results of SDS-PAGE show molecular weight thereof are respectively 68 kDa, 30 kDa and 21 kDa. Respectively, optimum reacting pH value, optimum reacting temperature, pH stable range, thermal stable range of chitinase are pH 5, 50° C., pH 5-7, and <60° C.; optimum reacting pH value, optimum reacting temperature, pH stable range, thermal stable range of chitosanase are pH 4, 50° C., pH 3-9, and <50° C.; and optimum reacting pH value, optimum reacting temperature, pH stable range, thermal stable range of nattokinase are pH 7, 50° C., pH 4-11, and <37° C. Activity of chitinase is inhibited by $Mn^{2+}$ and $Fe^{2+}$, activity of chitosanase is inhibited by $Mn^{2+}$, $Cu^{2+}$ and PMSF, and activity of nattokinase is completely inhibited by PMSF. Nattokinase belongs to serine-type protease, and $Fe^{2+}$ can increase its activity. Acetone can affect activity of chitinase, acetonitrile can affect activity of chitosanase, and ether can affect activity of nattokinase. With respect to organic solvent resistance, after placed for 10 days at 25° C. and 4° C., test results show that toluene, xylene and DMF don't affect activity of chitinase while the other organic solvents decrease activity of chitinase at 25° C., ether, acetonitrile and acetone can affect activity of chitinase; toluene, xylene and DMF don't affect activity of chitosanase while the other organic solvents decrease activity of chitosanase at 25° C., and ether and acetone can affect activity of chitosanase at 4° C.; and all the organic solvents don't affect activity of nattokinase.

Generally, shrimp and crab shell are useless and often thrown away. However shrimp and crab shell contains mass amount of protein and chitin, the present invention utilize a new strain TKU015 to ferment the shrimp and crab shell, and finally, valuable bioactive substance nattokinase can be produced, pollution to environment is reduced and value in use of shrimp shell castoff is improved.

The above description is given by way of example, and not limitation. Given the above disclosure, one skilled in the art could devise variations that are within the scope and spirit of the invention disclosed herein, including configurations ways of the recessed portions and materials and/or designs of the attaching structures. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A *Pseudomonas* sp. strain TKU015, which is deposited under DSMZ GmbH (Deutsche Sammlung von Mikroorganismen und Zellkulturen GmbH) as Deposit Number DSM 21747, and can be used to produce chitinase, chitosanase and nattokinase.

2. The *Pseudomonas* sp. strain TKU015 as claimed in claim 1, wherein the strain is selected from soil and cultured using shrimp shell powder as unique carbon/nitrogen source.

3. The *Pseudomonas* sp. strain TKU015 as claimed in claim 2, wherein the soil is dissolved in germfree water thereby obtaining a solution, the solution is coated on a solid culture medium comprising 0.2-1.5% by weight of shrimp shell powder (SSP), 0.05-0.2% by weight of $K_2HPO_4$, 0.02-0.1% by weight of $MgSO_4 \cdot 7H_2O$ and 0.5-3% by weight of agar, the culture medium is cultured a predetermined period thereby obtaining the *Pseudomonas* sp. strain TKU015.

4. A supernatant having chitinase, chitosanase and nattokinases activity obtained from a culture medium of *Pseudomonas* sp. strain TKU015, which is deposited under DSMZ GmbH (Deutsche Sammlung von Mikroorganismen und Zellkulturen GmbH) as Deposit Number DSM 21747.

5. The supernatant as claimed in claim 4, wherein the culture medium is liquid medium comprised of 0.2-1.5% by weight of shrimp shell powder (SSP), 0.05-0.2% by weight of $K_2HPO_4$, and 0.02-0.1% by weight of $MgSO_4 \cdot 7H_2O$, *Pseudomonas* sp. strain TKU015 is cultured in the liquid medium using a shaking culture method, and the supernatant is centrifugally separated from the liquid cultured medium.

6. The supernatant as claimed in claim 5, wherein the liquid medium is comprised of 0.5% by weight of shrimp shell powder (SSP), 0.1% by weight of $K_2HPO_4$, and 0.05% by weight of $MgSO_4 \cdot 7H_2O$, pH value of the liquid medium is 8, *Pseudomonas* sp. strain TKU015 is cultured in the liquid medium for 3 days at 30° C. using a shaking culture method thereby obtaining a fermented supernatant, the fermented supernatant is purified with ammonia sulfate precipitation thereby obtaining the supernatant.

7. A method of producing nattokinases, comprising:
fermenting a solution of aquatic products castoff powder containing chitin using a *Pseudomonas* sp. strain TKU015, which is deposited under DSMZ GmbH (Deutsche Sammlung von Mikroorganismen and Zellkulturen GmbH) as Deposit Number DSM 21747, thereby obtaining a supernatant; and
separating nattokinases from the supernatant.

8. The method of producing nattokinases as claimed in claim 7, wherein the aquatic products castoff comprises shrimp and crab shell, squid pen powder, mushroom and crude chitin.

9. The method of producing nattokinases as claimed in claim 7, wherein a concentration of the solution is in a range from 0.1% to 3%.

10. The method of producing nattokinases as claimed in claim 7, wherein the solution comprises 0.2-1.5% by weight of shrimp shell powder (SSP), 0.05-0.2% by weight of $K_2HPO_4$, and 0.02-0.1% by weight of $MgSO_4 \cdot 7H_2O$, the *Pseudomonas* sp. strain TKU015 is cultured in the solution using a shaking culture method.

11. The method of producing nattokinases as claimed in claim 10, wherein the solution comprises 1% by weight of shrimp shell powder (SSP), 0.1% by weight of $K_2HPO_4$, and 0.05% by weight of $MgSO_4 \cdot 7H_2O$, a volume of the solution is 100 mL, pH value of the solution is 7, the *Pseudomonas* sp, strain TKU015 is cultured in the solution for 2 days at 30° C. using a shaking culture method.

12. The method of producing nattokinases as claimed in claim 7, wherein the separating step comprises:
a. preparation of crude enzyme extract: the supernatant is processed with ammonia sulfate precipitation and centrifugal separation, remained sediments are re-dissolved in a phosphate buffer solution thereby obtaining a crude enzyme extract;
b. anion exchange chromatography: the crude enzyme extract is injected into a column for performing column chromatography, non-adsorbed protein is collected and then the column is eluted with phosphate buffer solution containing NaCl at a gradient of from 1 to 0 M NaCl such that adsorbed protein is eluted out, non-adsorbed area is collected as nattokinase solution; and
c. hydrophobic chromatography: nattokinase solution is injected into a column and the column is eluted with phosphate buffer solution containing ammonium sulfate, hydrophobicity of the column is gradually changed such that nattokinases can be separated.

* * * * *